US005843481A

United States Patent [19]
Cruz

[11] Patent Number: 5,843,481
[45] Date of Patent: Dec. 1, 1998

[54] TREATMENT OF PROLIFERATIVE DISORDERS, METASTASAES, AND DRUG RESISTANT TUMORS WITH VANADATE COMPOUNDS AND DERIVATIVES OR ANALOGUES THEREOF

[75] Inventor: Tony Cruz, Etobicoke, Canada

[73] Assignee: Mount Sinai Hospital Corporation, Toronto, Canada

[21] Appl. No.: 181,980

[22] Filed: Jan. 18, 1994

[51] Int. Cl.$^6$ ............................ A61K 33/24; A61K 31/28
[52] U.S. Cl. ............................................ 424/646; 514/492
[58] Field of Search .............................. 514/492; 424/646

[56] References Cited

U.S. PATENT DOCUMENTS

| | | | |
|---|---|---|---|
| 4,882,171 | 11/1989 | Posner et al. | 424/616 |
| 5,001,141 | 3/1991 | Kerr et al. | 514/398 |
| 5,009,891 | 4/1991 | Niwa et al. | 424/195.1 |
| 5,023,358 | 6/1991 | Lazaro et al. | 556/42 |
| 5,036,096 | 7/1991 | Suto | 514/398 |
| 5,045,316 | 9/1991 | Kaplan | 424/400 |
| 5,069,913 | 12/1991 | Posner et al. | 424/646 |
| 5,073,639 | 12/1991 | Suto | 548/339 |
| 5,175,001 | 12/1992 | Lazaro et al. | 424/451 |
| 5,527,790 | 6/1996 | McNeill | 514/186 |
| 5,545,661 | 8/1996 | Cullinan | 514/460 |
| 5,565,491 | 10/1996 | Schieven | 514/492 |
| 5,583,242 | 12/1996 | Schieven | 556/44 |

FOREIGN PATENT DOCUMENTS

| | | |
|---|---|---|
| 0 264 278 | 4/1988 | European Pat. Off. |
| 524633 | 1/1993 | European Pat. Off. |
| 641045 | 2/1984 | Switzerland . |
| 2194885 | 3/1988 | United Kingdom . |
| PCT/US 95/01234 | 8/1995 | WIPO . |

OTHER PUBLICATIONS

Sardar, S.A., et al., Biol. Abstr. 95(10)AB–802, 110965, 1995.
Sakurai, H. 2nd Internat. Meeting on Molecular Mechanisms of Metal Toxicity, Jan. 10–17, 1993.
Dessureault, J. and Weber, J. Cell Biochem. 43:293–296, 1990.
Klarlund, J. et al., Biochim. Biophys. Acta. 971 112–120, 1988.
Keiler, J. et al., Acta Chirurgica Scandinavica–Supplementum, 343:154–64, 1965.
Stern et al., Biochem. Cell. Biol., 71:103, 1993.
William Lau, C.H. et al, Endocrinology, 123:2858, 1988.
Marchisio, P.C. et al., J. Cell. Biol. 37:151, 1988.
Wang and Scott, J. Cell, Physiol. 158:408–416, 1994.
Xuefeng Yin, et al., Molecular and Cellular Biochemistry 115:85–96, 1992.
Conquer, J.A. et al., 39th Annual Meeting, Orthopaedic Research Society, Feb. 15–18, 1993, San Francisco, CA.
Cruz, T. et al., Molecular and Cellular Biochemistry 153:161–166, 1995.
Conquer, J., et al., Annals N.Y. Acad. Sci. Sep. 1994, p. 447.
Wang and Scott, Mol. Cell. Biol. 153:59–67, 1995.
Younes, M. et al., Toxicology 66(1):63–74, 1991.
Sardar, S. et al., Tumor Research 28:51–61, 1993.
Younes, M. et al., Toxicology 7:141–149, 1991.
Sakurai, H. et al., Biochem Biophys Res Commun, 189(2):1090–1095, 1992.
Hanauske, U. et al., Int J Cell Cloning, 5(2):170–178, 1987.
Thompson, H.J. et al., Carcinogenesis, 5(6):849–851, 1984.
Bishayee, A. et al., Acta Physiol. Pharmacol. Bulg, 19/3:83–89, 1993.
A. Petkau, Br. J. Cancer, 55:87–95, 1987.
C. Norman Coleman, Seminars in Oncology 16:169–175, 1989.
Alvarez et al., J. Natl. Cancer Inst. 82(7):589–595, 1990.
Schultz et al., Cancer Res. 48, 5539–5545, 1988.
Wang & Stearns, Cancer Res. 48, 6262–6271, 1988.
Saxena et al., Biochem. Pharmacology 45(3): 539–542, 1993.
Shklar et al., Nutrition and Cancer, 20(2):145–151, 1993.
Kandel et al., Biochim. Biophys. Acta. 1053, 130–134, 1990.
Conquer, Biochim. Biophys. Acta. 1134, 1–6, 1992.
Cruz et al., Biochem. J. 277:327–330, 1991.
Slaga and Bracken, Cancer Research 37:1631–1635, 1977.
Clark, Pathology 18:181–186, 1986.
Schor, Biochem. Pharm. 37(9):1751–1761, 1988.
Fridovich, "Superoxide Dismutase in Biology and Medicine" in Pathology of Oxygen, American Press, Inc., Chapter 1, pp. 1–19, 1982.
Marklund et al., "Oxy–Radicals in the Toxicity of Cellular Toxins" in Oxy Radicals and Their Scavenger Systems, vol. II: Cellular and Medical Aspects, by Elsevier Science Publishing Co., Inc., pp. 96–104, 1983.
Machlin and Bendich, FASEB, 1:441–445, 1987.
Southorn and Powis, Mayo Clin. Proc. 63:381–388, 1988.
McLennan et al., Radiation Research, 84:122–132, 1980.
Scott et al., J. Biol. Chem., 264(5):2498–2501, 1989.
Edsmyr, Pathology of Oxygen, *Superoxide Dismutase Efficacy in Ameliorating Side Effects of Radiation Therapy: Double–Blind, Placebo–Controlled Trials in Patients with Bladder and Prostate Tumors,* in Chapter 19, pp. 315–326, Academic Press, Inc. 1982.
Thompson et al., Carcinogenesis, vol. 5, No. 6, pp. 849–851, 1984.
Hamada et al., Cancer Research, 48(17), 4926–32, 1988.
Ishikaiva et al., J. Biol. Chem. 268(27), 20116–25, 1993.

*Primary Examiner*—Phyllis G. Spivack
*Attorney, Agent, or Firm*—Bereskin & Parr

[57] ABSTRACT

The present invention relates to the use of vanadate compounds, or analogues of vanadate compounds, as antiproliferative and anti-metastatic agents, and to compositions containing vanadate compounds adapted for such use in methods for the treatment of proliferative disorders, methods of reducing the ability of a tumor to metastasize and methods for treating drug resistant tumors.

10 Claims, 20 Drawing Sheets

TREATMENT OF PROLIFERATIVE DISORDERS, METASTASAES, AND DRUG RESISTANT TUMORS WITH VANADATE COMPOUNDS AND DERIVATIVES OR ANALOGUES THEREOF

FIELD OF THE INVENTION

The present invention relates to the use of vanadate compounds or derivatives or analogues of vanadate compounds as antiproliferative and anti-metastatic agents, and/or to treat drug resistant tumors in animals; to compositions containing vanadate compounds adapted for such use; to methods for the treatment of proliferative disorders, to methods of reducing the ability of a tumor to metastasize, and to methods for treating drug resistant tumors. The invention also relates to methods for testing for substances which affect cell proliferation.

BACKGROUND OF THE INVENTION

Cancer is a global problem which affects an estimated 5.9 million people worldwide annually. There are many types of cancer, some of the most common in North America include breast, lung, colon and lymphatic cancer. Although chemotherapy has had positive impact on the survival rate of cancer patients in the last 30 years, most human cancers are, or become resistant to chemotherapy. Thus, there is a tremendous need for anticancer drugs which are more effective and which can act on drug resistant tumors.

Two important features of cancer cells is their ability to proliferate abnormally leading to tumor formation and growth, and to invade other tissues leading to metastases. It is thought that genetic damage to specific genes is responsible for the transformation of cells and the development of cancer in humans. The genetic damage found in human cancer cells can be divided into two types. One of these involves the mutation of oncogenes which results in continuous proto-oncogene activation. The second involves the mutation of tumor suppressor genes which results in the loss of their function. Genetic damage to proto-oncogenes or to tumor suppressor genes leads to oncogene activation in the absence of stimuli and to uncontrolled cellular proliferation. Damage has been found to one or another proto-oncogenes and tumor suppressor genes with some consistency in a variety of human malignancies.

Two oncogenic transcription factors, fos and jun, have been shown to be involved and required for the induction of genes involved in cellular proliferation and in particular, in cellular proliferation in many tumor cell lines. Inhibition of the expression of these two genes leads to the inhibition of cellular proliferation.

One of the most life threatening aspects of cancer is the development of metastases. Generally, most solid tumors can be removed surgically from the primary site resulting in a local cure. However, if the cancer cells have invaded vascular channels and metastasized to a different organ, then the likelihood of a complete cure is reduced. Thus, agents which reduce the metastatic properties of cancer cells would be beneficial for the treatment of cancer.

The cellular processes thought to play an important role in metastases include; increased cellular attachment, tumor cell proteolysis of host tissue, tumor cell locomotion and colony formation. These processes occur in a sequential order. First, tumor cells attach to the basement membrane through their surface receptors of integrin and non-integrin types to ligands such as collagen, laminin and fibronectin in the basement membrane. After attachment, a localized zone of lysis of the basement membrane occurs at the point of cell attachment. The tumor cells produce and secrete degradative enzymes, such as collagenase and gelatinase, which degrade the basement membrane and allow the infiltration and locomotion of tumor cells into the host organ. There is a positive association between tumor aggessiveness and the ability of cells to produce a group of enzymes, matrix metalloproteases, involved in the invasive process. Inhibition of certain proteases, such as metalloproteases or serine proteases, have been shown to prevent invasion and metastasis (Alvarez et al. 1990. J. Natl. Cancer Inst. 82: 589–595; Schultz et al 1988, Cancer Res. 48, 5539–5545; and, Wang & Stearns 1988, Cancer Res. 48, 6262–6271)).

Ionic vanadium compounds such as vanadyl or vanadate salts in combination with thiosulphate or sulfite compounds have been reported to be useful for treating malignant tumors, arteriosclerosis and mental syndromes in the elderly ((U.S. patent Ser. No. 5,045,316 to Kaplan). Kaplan discloses a daily dose ranging from 0.0043 mg/kg to 0.14 mg/kg of vanadyl or vanadate salts. No mechanism for the action of vanadate and thiosulphate in the disclosed treatments is provided by Kaplan.

In the background of the Kaplan patent it is disclosed that others have reported that vanadium salts have an antineoplastic effect and dietary vanadyl sulphate has been reported to inhibit chemically induced mammary carcinogenesis in rats.

Saxena et al. (Biochem. Pharmacology 45(3): 539–542, 1993) examined the in vivo effects of vanadate on the antioxidant status of control and alloxan diabetic rat livers. Diabetic rats were administered 0.6 mg sodium orthovanadate/ml in drinking water. It should be noted that the present inventor has found that oral administration of orthovanadate to animals at 0.5 mg/ml results in gastric toxicity (See Example 9 herein).

Antioxidants such as $\beta$-carotene, $\alpha$-tocopherol, vitamin E, vitamin C, and glutathione have been reported to have anticancer activity (G. Shklar et al. Nutrition and Cancer, 1993, p.145). It has also been disclosed that a mixture of antioxidants ($\beta$-carotene, dl-$\alpha$-tocopherol acid succinate (vitamin B), vitamin C, and reduced glutathione) was very effective in preventing carcinogenesis in an in vivo cancer model and was more effective than the individual components of the mixture as cancer chemopreventive agents.

SUMMARY OF THE INVENTION

The present inventor has found that the levels of superoxides or $H_2O_2$ in the cell play an important role in the induction of fos and jun expression. Reducing the levels of $H_2O_2$ by inhibiting its production with diphenyl iodonium (DPI), or by increasing the levels of intracellular reducing agents such as N-acetylcysteine and orthovanadate were shown to completely inhibit fos and Jun expression in response to factors such as IL 1 or arachidonic acid. Under all of the conditions examined, inhibition of fos and jun expression results in inhibition of collagenase expression.

The present inventor also found that orthovanadate and its analogues are extremely toxic to proliferating cell lines, at concentrations that are not toxic to normal nonproliferating cells indicating that orthovanadate may be useful as a chemotherapeutic agent. He has also significantly found that orthovanadate acts on cell lines resistant to conventional drugs such as colchicine, vinblastine and doxorubicin indicating that the drug is useful for treatment of drug resistant tumors. The mechanisms which normally expel chemotherapeutic agents from cancer cells that are drug resistant do not recognize the vanadate compounds.

Orthovanadate and analogues thereof were also shown to suppress tumor growth in an in vivo animal model (MDAY-D2 model). Doses of at least 0.2 mg/kg were required to reach concentrations of orthovanadate or analogues thereof in the serum of the animals to be highly toxic to cancer cells.

Significant inhibition of tumor growth was observed when orthovanadate in combination with an anti-oxidant, N-acetylcysteine, was administered. The action of orthovanadate and N-acetylcysteine was more effective in inhibiting tumor growth in vivo than orthovanadate alone.

The present inventor also found that animals receiving orthovanadate or vanadyl sulphate did not have detectable levels of metastases.

Accordingly, broadly stated the present invention relates to a method of modulating fos and jun expression by regulating concentrations of hydrogen peroxide.

In accordance with an embodiment of the invention compounds are used to reduce hydrogen peroxide and/or superoxides to thus effect a reduction in cell proliferation. Preferably the compounds are vanadate compounds, or derivatives or analogues thereof.

The invention also contemplates a pharmaceutical composition for the treatment of proliferative disorders comprising an amount of a vanadate compound, or a derivative or an analogue thereof, effective to reduce cell proliferation, and one or more of a pharmaceutically acceptable carrier, diluent, or excipient. In a preferred embodiment of the invention, the pharmaceutical composition is used to reduce tumor growth. The invention further contemplates a method for the treatment of a proliferative disorder comprising administering an amount of a vanadate compound, or a derivative or an analogue thereof, effective to reduce cell proliferation.

The amount of a vanadate compound or derivative or analogue thereof, effective to reduce cell proliferation is an amount which results in a serum concentration of the compound of at least 5 $\mu$M, preferably 5–50 $\mu$M, most preferably 10–30 $\mu$m. Generally a dosage of at least 0.2 mg/kg, preferably 0.2 mg/kg to 20 mg/Kg will result in the-appropriate serum concentrations in humans and other mammals.

The invention also relates to a method for reducing or inhibiting the growth of drug resistant tumors comprising administering an amount of a vanadate compound, or a derivative or an analogue thereof effective to reduce or inhibit the growth of drug resistant tumors. The invention further contemplates a method for reducing or inhibiting metastases comprising administering an amount of a vanadate compound, or a derivative or an analogue thereof effective to reduce or inhibit metastases.

The invention also contemplates a composition comprising a vanadate compound or a derivative or analogue thereof, and at least one antioxidant, preferably N-acetylcysteine, which enhances the antiproliferative and anti-metastatic effects, of the vanadate compound and reduces cell proliferation and metastases. Methods of treating and preventing proliferative disorders, treating drug resistant tumors, and reducing metastases using this composition are also provided.

The invention also relates to methods for testing a drug for activity in reducing cell proliferation.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

Further details of the invention are described below with the help of the examples illustrated in the accompanying drawings in which.

DETAILED DESCRIPTION OF THE INVENTION

Figure 1:
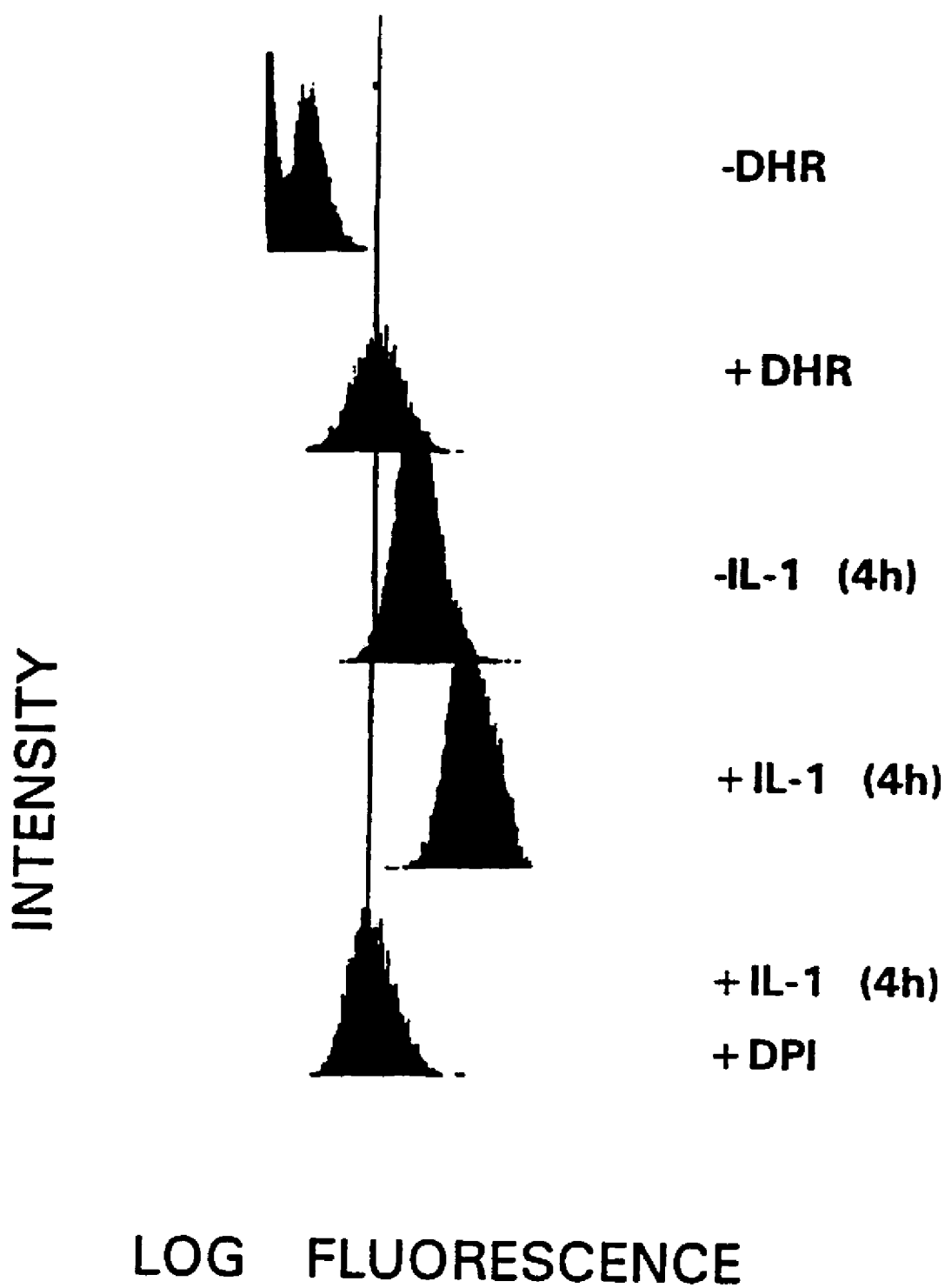
FIG. 1 is a graph showing the FACS analysis of superoxide production in response to IL 1 and inhibition of NADPH oxidase by DPI.

As hereinbefore mentioned, the present invention relates to a method of modulating fos and Jun expression by regulating concentrations of hydrogen peroxide. Increasing the concentrations of hydrogen peroxide should result in increased expression of fos and jun and accordingly an increase in cell proliferation. An increase in cell proliferation would be useful in the treatment of conditions involving damaged cells and in particular may be useful in treating conditions in which degeneration of tissue occurs such as arthropathy, bone resorption, inflammatory disease, degenerative disorders of the central nervous system, and for promoting wound healing.

In accordance with an embodiment of the invention compounds are used to reduce hydrogen peroxide and/or superoxides to thus effect a reduction in cell proliferation. Preferably the compounds are vanadate compounds, or derivatives or analogues thereof. Suitable vanadate compounds for use in the present invention are oxidative forms of vanadate, preferably orthovanadate. Derivatives of vanadate compounds, preferably pharmaceutically acceptable salts, esters and complexes of vanadate compounds including potassium and sodium salts, and amino acid, carbohydrate and fatty acid complexes, for example, vanadate complexed with cysteine, dihydroxamate, and glucuronate may also be used in the present invention.

Suitable analogues may be selected based upon their functional similarity to vanadate compounds, including the ability to interact with hydrogen peroxide to produce hydroxyl radicals or to generally reduce hydrogen peroxide. Examples of such compounds include metal ions such as iron, titanium, cobalt, nickel and chromium complexes, stannum, glutathione, and diphenyl iodonium. Analogues of vanadate compounds may also be selected based upon their three dimensional structural similarity to vanadate compounds. For example, the vanadyl forms of vanadium may be used in the present invention, preferably vandyl sulphate.

Most preferably, orthovanadate and vanadyl sulphate are used in the pharmaceutical compositions, therapeutic treatments and methods of the present invention.

Selected derivatives and analogues of vanadate compounds may be tested for their ability to reduce hydrogen peroxide, their ability to effect growth of proliferating cell lines, non-proliferating cell lines, and drug resistant cell lines, and their ability to inhibit tumor growth or metastases in animal models following the methods described herein.

The composition of the invention may contain one of more antioxidants in combination with a vanadate compound or analogue or derivative thereof. The antioxidant(s) are selected based on their ability to increase the efficacy of the vanadate compounds and reduce toxicity on normal cells using the methods described herein. Suitable antioxidants for use in the enhancing composition of the invention include N-acetylcysteine, glutathione, Vitamin E (alpha-tocopherol), Vitamin C (ascorbic acid), beta-carotene, ergothioneine, zinc, selenium, copper, manganese, flavonoids and estrogens, or derivatives thereof, preferably N-acetylcysteine.

The administration of vanadate compounds or analogues or derivatives thereof, and optionally one or more antioxidants, in the forms and modes described herein reduces hydrogen peroxide to effect a reduction in cell proliferation, and also reduces metastases of tumors. Thus, the compositions may be used for the treatment of proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections. The compositions of the invention have been shown to be specifically effective in inhibiting the growth of hematopoietic tumors, human glioma and astrocytoma primary tumors.

Vanadate compounds or analogues or derivatives thereof, and optionally one or more antioxidants, in the compositions described herein may also be used to treat drug resistant tumors. Examples of drug resistant tumors are tumors expressing high levels of P-glycoprotein which is known to confer resistance to multiple anticancer drugs such as colchicine, vinblastine and doxorubicin, or tumors expressing the multi-drug resistance protein as described in R. Deeley et al., Science, 258:1650–1654, 1992.

The compositions of the invention contain vanadate compounds or derivatives or analogues thereof, and optionally one or more antioxidants, either alone or together with other substances. Such pharmaceutical compositions can be for topical, parenteral (intravenous, subcutaneous, intramuscular or intramedullary) or local use. Preferably, a mode of administration is used which results in a slow continuous release of the active substances. This may be achieved by intravenous administration, subcutaneous administration, or using control release mechanisms such as implants or pumps. Control release methods generally use control release polymers and the release of the active ingredient is based on solubility properties, and the pore size of the polymers and active ingredients.

In the case of parenteral administration, solutions, suspensions, emulsions or powders of the vanadate compound and/or derivative and or analogue thereof, and optionally antioxidant(s) can be employed, using one or more pharmaceutically acceptable excipients or diluents, suitable for the aforesaid uses and with an osmolarity which Is compatible with the physiological fluids. For local use, those preparations in the form of creams or ointments for topical use or in the form of sprays should be considered.

The preparations of the invention can be intended for administration to humans and various other mammals, such as ovines, bovines, equines, swine, canines, and felines.

The amount of a vanadate compound or derivative or analogue thereof, effective to reduce cell proliferation, and/or to reduce metastases or treat drug resistant tumors is the minimum dose adequate to achieve a reduction in cell proliferation, reduction or inhibition of metastases, and/or growth of drug resistant tumors. A dose which results in a serum concentration of the compound of at least 5 $\mu$M, preferably 5–50 $\mu$M, most preferably 10–30 $\mu$M, is required to reduce cell proliferation and accordingly provide for effective treatment of proliferative disorders. Generally, a dose of at least 0.2 mg/kg, preferably 0.2 mg/kg to 20 mg/Kg will provide an appropriate serum concentration in humans and other mammals. The above-mentioned doses may be used to reduce metastases and treat drug resistant tumors. The selected doses will also depend on individual needs and the mode of administration.

When the vanadate compound or analogue or derivative thereof is used in combination with one or more antioxidants, the doses of the vanadate compound or analogue or derivative thereof and the antioxidant(s) are selected so that the vanadate compound and antioxidant(s) alone would not show a full effect. Generally, the effective doses of the vanadate compound and the antioxidant(s) are the minimum doses adequate for enhanced antiproliferative or anti-metastatic effects. The vanadate compound and antioxidant(s) may be administered concurrently, separately, or sequentially.

The vanadate compound and antioxidant may be prepared and administered as a complex. For example, vanadate may be complexed with glutathione or N-acetylcysteine.

In an embodiment of the invention, a dose of orthovanadate compound is administered which provides a serum concentration of the compound of at least 5 $\mu$M, preferably 5–50 $\mu$M, most preferably 10–30 $\mu$M. N-acetylcysteine is administered prior to, (preferably 20 minutes prior to), and during administration of orthovanadate, at a dose which provides a serum concentration of the compound of between 0.5 mM to 15.0 mM, preferably 5 mM to 12.5 mM. Generally, a dose of between 40.0 mg/kg to 1000 mg/Kg of N-acetylcysteine will provide an appropriate serum concentration in humans and other mammals.

The compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the vanadate compounds, derivatives or analogues thereof in association with one or more pharmaceutically acceptable vehicles or diluents, and contained in buffered solutions with a suitable pH and iso-osmotic with the physiological fluids.

The compositions and treatments are indicated as therapeutic agents or treatments either alone or in conjunction with other therapeutic agents or other forms of treatment. In particular, the compositions and treatments described herein may be used to reduce toxicity of other therapeutic agents. For example the compositions of the invention may be used in combination with radiotherapy or chemotherapy, such as multi-drug chemotherapy for Hodgkins disease or combination radiotherapy, and chemotherapy for treatment of breast cancer.

As hereinbefore mentioned the invention also relates to methods for assaying for substances that affect cell proliferation. The method involves determining the effect of the substance on the growth of non-proliferating cells and comparing the effect to that observed for the substance with proliferating cells. In one embodiment a substance which is suspected of affecting cell proliferation is assayed by preparing a non-proliferating primary cell culture by plating non-proliferatlng preferably human or bovine chondrocytes or fat cells, at high cell density, preferably $2 \times 10^6$ to $4 \times 10^6$ cells/per well on a six well plate, and preparing a proliferating cell culture by plating proliferating cells, preferably chondrocytes at low density preferably $5 \times 10^5$ to $1 \times 10^6$ cells/per well on a six well plate; incubating each of the cell cultures in media containing the substance suspected of affecting cell proliferation preferably for 1 to 48 hours at about 37° C., harvesting cells and quantitating the number of viable cells, and comparing the number of viable cells in the proliferating and non-proliferating cell cultures.

The following non-limiting examples are illustrative of the present invention:

EXAMPLES

Example 1

Identification of Signalling Mechanisms Regulating Fos, Jun and Collagenase Expression The sequence of events or second messengers responsible for the stimulation of fos and jun expression were investigated.

A. IL 1 induces a transient increase in fos and Jun mRNA.

The cytokine interleukin 1 (IL 1) has been used to identify the intermediate second messengers which regulate the expression of fos and jun. The reason for using IL 1 is that it has been shown to stimulate fos and jun expression, and produce all of the signals required to induce the expression of matrix metalloproteases. IL 1 was found to induce a transient increase in fos and jun mRNA levels which peaks by 30 min to one hour, whereas the appearance of collagenase mRNA is detected by 9 hours and continues to increase up to 12 hours. This data is consistent with studies demonstrating that fos and jun expression is required for collagenase production.

B. IL 1 stimulates the production of reactive oxygen intermediates

Chondrocytes (i.e. bovine chondrocytes plated as described in Kandel R. A. et al. Biochim. Biophys. Acta. 1053, 130–134, 1990) were incubated with dihydroxyrhodamine for 5 min (DHR) or for 4 hours in the absence (–IL 1) or presence of IL 1 (+IL 1), or in the presence of both IL 1 and the NADPH inhibitor, diphenyl iodonium, (+IL 1, +DPI). FIG. 1 shows that IL 1 stimulates the production of reactive oxygen intermediates by FACS analysis. The inhibitor of NADPH oxidase, DPI (diphenyl iodonium), completely inhibits constitutive and IL 1 induced reactive oxygen intermediates in chondrocytes. These data indicate that IL 1 stimulates the production of intracellular superoxides and oxygen reactive intermediates.

C. Effect of DPI on fos and jun mRNA levels induced by IL 1

Figure 2:
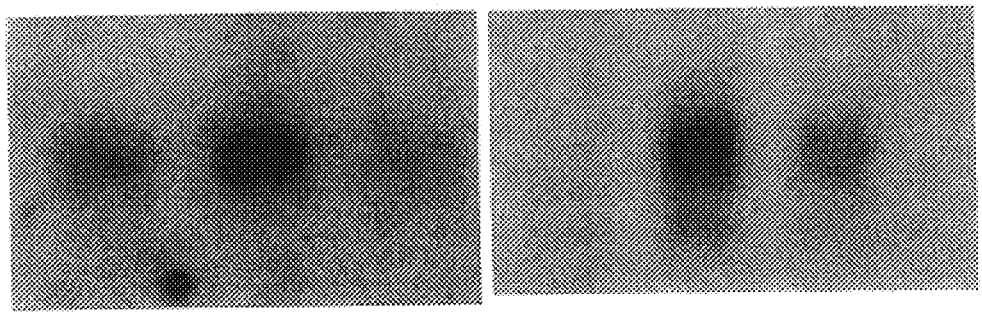
FIG. 2 is a Northern Blot showing the role of superoxide production on fos and collagenase expression.

Although IL 1 stimulated superoxide production, it was not known whether IL 1 induced fos and jun expression was dependent on the production of superoxides. In order to elucidate this possibility, the effect of DPI on fos and jun mRNA levels induced by IL 1 was investigated. RNA from chondrocytes treated with IL 1 in the presence and absence of DPI were analyzed by Northern blot analysis using either fos or collagenase cDNA probes. The results demonstrated that IL 1 induction of fos and collagenase is suppressed by DPI, indicating that superoxide production plays a role in the induction of these genes (FIG. 2). Similar data has been obtained for IL 1 induced jun expression. Furthermore, inhibition of fos and jun expression by DPI was sufficient to suppress IL 1 induced and constitutive collagenase expression. These data indicate that inhibition of superoxides or $H_2O_2$ production prevents the induction of fos, jun and collagenase expression.

Figure 3:
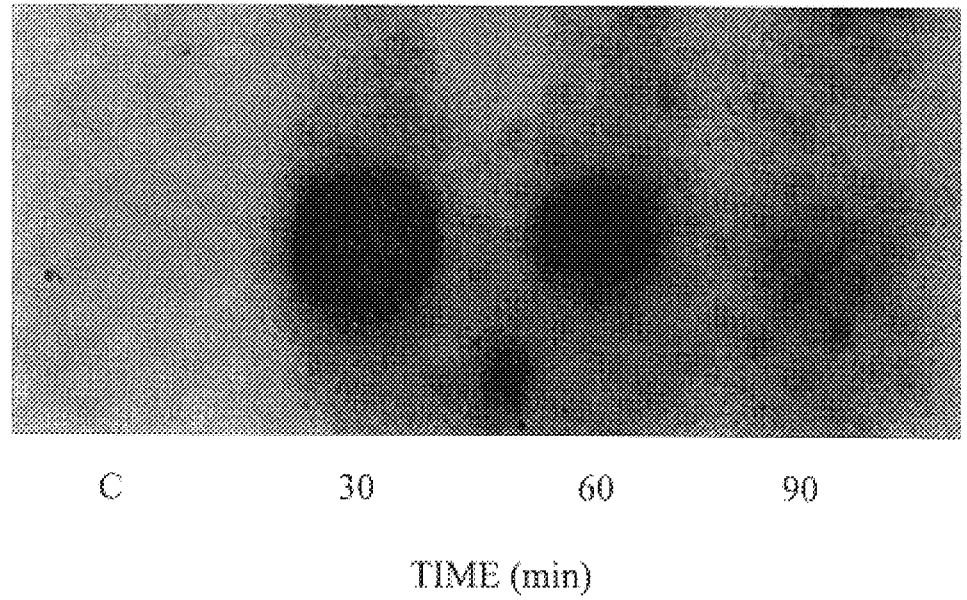
FIG. 3 is a Northern blot showing hydrogen peroxide stimulates fos expression.

D. Hydrogen peroxide mimics the effect of IL 1 in the induction of fos expression Since superoxides are rapidly converted to hydrogen peroxide in the cell by superoxide dismutase, whether hydrogen peroxide could mimic the effect of IL 1 in the induction of fos expression was investigated. RNA was extracted from chondrocytes (Kandel et al. supra) treated with $H_2O_2$ for 30, 60 and 90 minutes and examined by Northern blot analysis using a fos cDNA probe. As demonstrated in FIG. 3, addition of $H_2O_2$ to chondrocytes also stimulates the expression of fos, suggesting that this molecule may be a key second messenger in the induction of the transcription factors, fos and jun.

E. Effect of orthovanadate and N-acetylcysteine on fos, jun and collaganase expression The effect of orthovanadate and N-acetylcysteine on fos, jun and collagenase expression were examined.

Bovine articular chondrocytes were isolated and plated as previously described (Kandel R. A. et al. Biochim. Biophys. Acta. 1053, 130–134, 1990). In order to determine the effect of orthovanadate on IL 1 and PMA (phorbol ester) induced responses, chondrocytes were incubated with orthovanadate (100 $\mu$M) for 2 hours before stimulation with IL 1 (10 ng/ml)

or PMA (100 mg/ml). collagenase production was determined by incubating chondrocytes for 24 hours with IL 1 or PMA and the cell conditioned medium was assayed for collagenase activity using an ELISA procedure as described previously (Kandel et al. supra) $PLA_2$ activity was measured by incorporating $^3$H-arachidonic acid ($^3$H-AA) into the cells and then incubating the cells with medium containing 1 mg/ml BSA, either alone or in the presence of IL 1 or PMA, for 10 min. as previously described (Conquer, J. A. 1192, Biochim. Biophys. Acta. 1134, 1–6). The amount of $^3$H-AA liberated into the supernatant was determined. To measure $PGE_2$ production, chondrocytes were incubated for 6 hours in Ham's F12 medium, either alone or with IL 1 or PMA. The supernatant was analyzed by RIA using an antibody specific for $PGE_2$ (Dr. S. A. Jones, Mount Sinai Hospital, Toronto, Can.). In order to examine the expression of c-fos and c-jun, chondrocytes were incubated for 1 hour in the presence of IL-1, PMA or AA (3 $\mu$M). Chondrocytes were washed in PBS and the total RNA extracted as previously described (Cruz. et al, 1991, Biochem. J. 277, 327–330). RNA samples were run on formaldehyde agarose gels and transferred to nylon membrane for northern analysis using cDNA probes for c-fos and c-jun.

Figure 4:
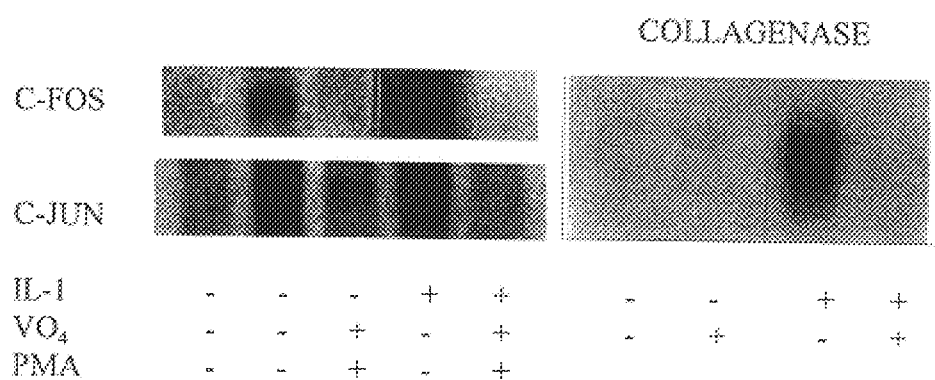
FIG. 4 is a Northern blot showing that orthovanadate inhibits fos, jun and collagenase expression.
Figure 18:
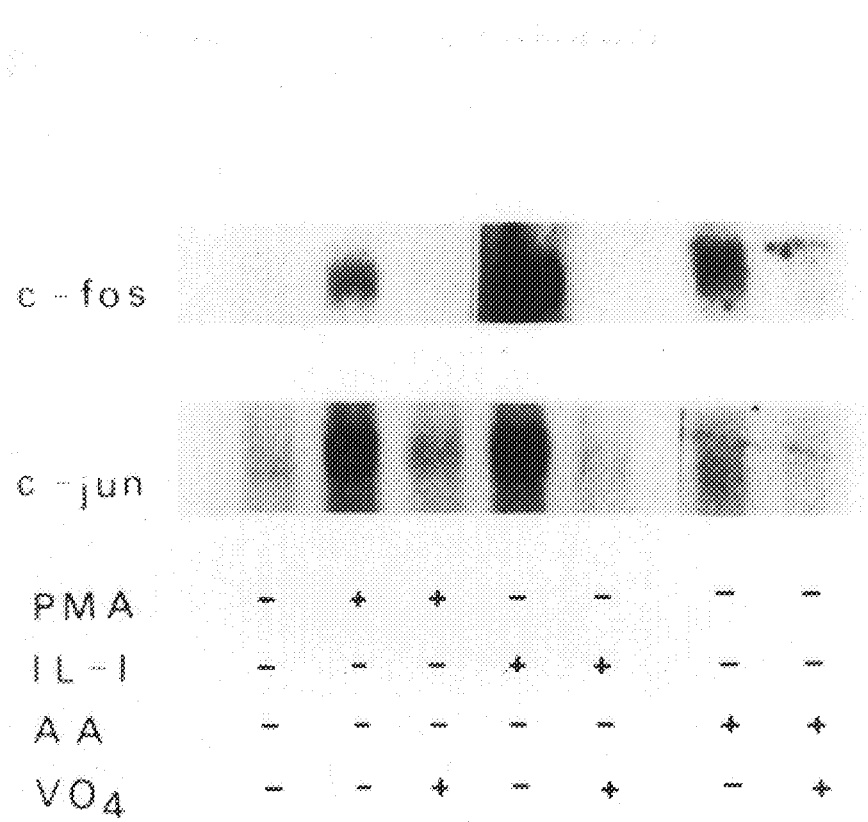
FIG. 18 is a Northern blot showing orthovanadate inhibition of IL 1, PMA and AA induced c-fos and c-jun expression.

IL 1 and PMA induced the release of $^3$H-AA as well as the production of $PGE_2$ and collagenase by chondrocytes in monolayer culture. Although orthovanadate (100 uM) completely inhibited the production of collagenase it did not inhibit the IL 1 or PMA induced release of $^3$H-AA or the production of $PGE_2$. These data would suggest that either the effect of orthovanadate is occurring downstream from $^3$H-AA release or that the mechanisms regulating $PLA_2$ activity and $PGE_2$ production are separate from those regulating collagenase production. The expression of c-fos and c-jun were stimulated by IL 1, PMA as well as AA itself in bovine chondrocytes. Orthovanadate completely inhibited the IL 1, PRA and AA induced c-fos and c-jun expression, which may be responsible for the inhibition of collagenase production. These data (See FIGS. 4 and 18) suggest that orthovanadate inhibition of collagenase production may be occurring downstream from the IL 1 induced $^3$H-AA release by inhibiting c-fos and c-jun expression in chondrocytes. The data demonstrating that orthovanadate is a potent inhibitor of fos, jun and collagenase expression indicates that agents reducing $H_2O_2$ levels in cells may serve as potent inhibitors of expression of fos and jun.

Figure 5:
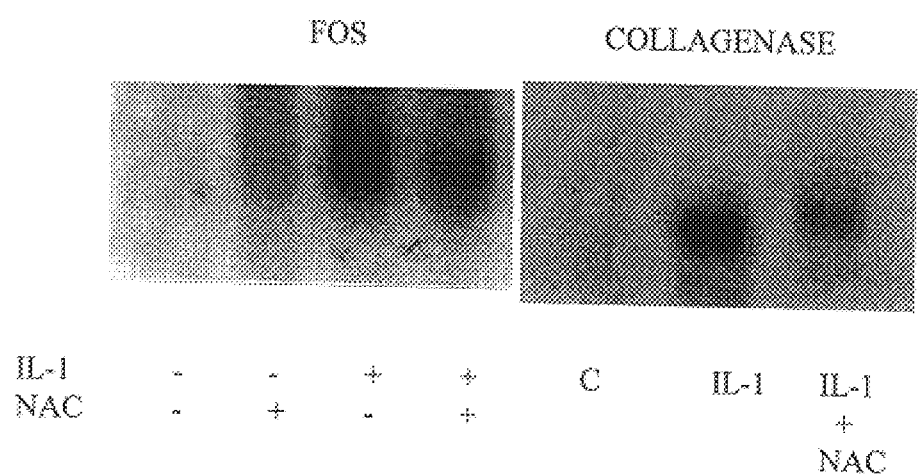
FIG. 5 is a Northern blot showing N-acetylcysteine inhibits IL 1 induction of fos and collagenase expression.

Cells were also incubated as described above with 20 mM N-acetylcyateine for 20 min. and then incubated with IL 1 for an additional 1 or 12 hours. The RNA was extracted and examined by Northern blot analysis using cDNA probes for c-fos and collagenase. N-acetylcysteine which is converted to GSH intracellularly was also found to reduce the levels of fos and collagenase expression in response to IL 1 (FIG. 5). Presumably the higher intracellular levels of GSH reduced $H_2O_2$ and superoxide levels and suppressed the induction of fos and collagenase expression.

In summary, the results demonstrate that both N-acetylcysteine and orthovanadate indirectly reduce the levels of superoxides and $H_2O_2$ in cells.

Example 2

Vanadate Compounds as Potent Chemotherapeutic Agents in Vitro

The effect of a class of vanadyl derivatives, on cellular proliferation in vitro is described below.
A. In vitro effects of Vanadyl Derivatives on normal non-proliferating and proliferating cells.

As described in example 1, orthovanadate inhibited fos, jun and collagenase expression. If fos and jun expression are required for cellular proliferation, then orthovanadate should inhibit chondrocyte proliferation. In order to compare the effect of orthovanadate on non-proliferating and proliferating chondrocytes, chondrocytes were plated at both high cell density ($2 \times 10^6$ to $4 \times 10^6$ cells/per well on a six well plate) (nonproliferating) and at a lower cell density ($5 \times 10^5$ to $1 \times 10^6$ cells/per well on a six well plate) (proliferating) and then maintained for 48 hours. The cells were then incubated in media (HAMS F12) containing 0–50 $\mu$M Orthovanadate for an additional 48 hours. The cells were harvested and the number of viable cells determined.

Figure 6:
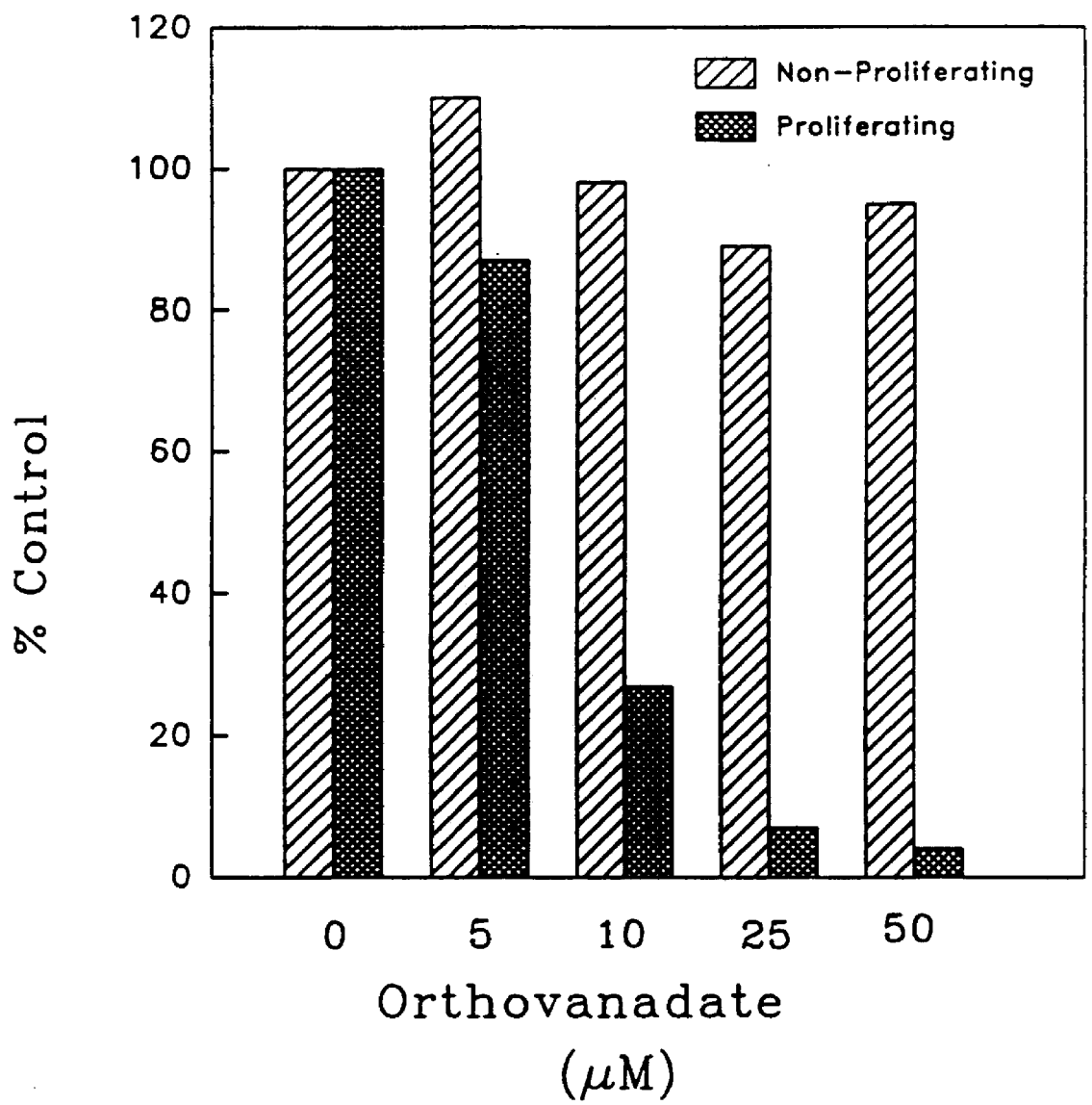
FIG. 6 is a graph showing the effect of orthovanadate on proliferating cells.

FIG. 6 demonstrates that orthovanadate did not effect the chondrocytes that were plated at high cell density but was toxic to cells plated at low cell density. These data suggest that proliferating cells are sensitive to orthovanadate, whereas non-proliferating cells are resistant to orthovanadate toxicity.

B. In vitro effects of orthovanadate on proliferating tumor cell lines

Figure 7:
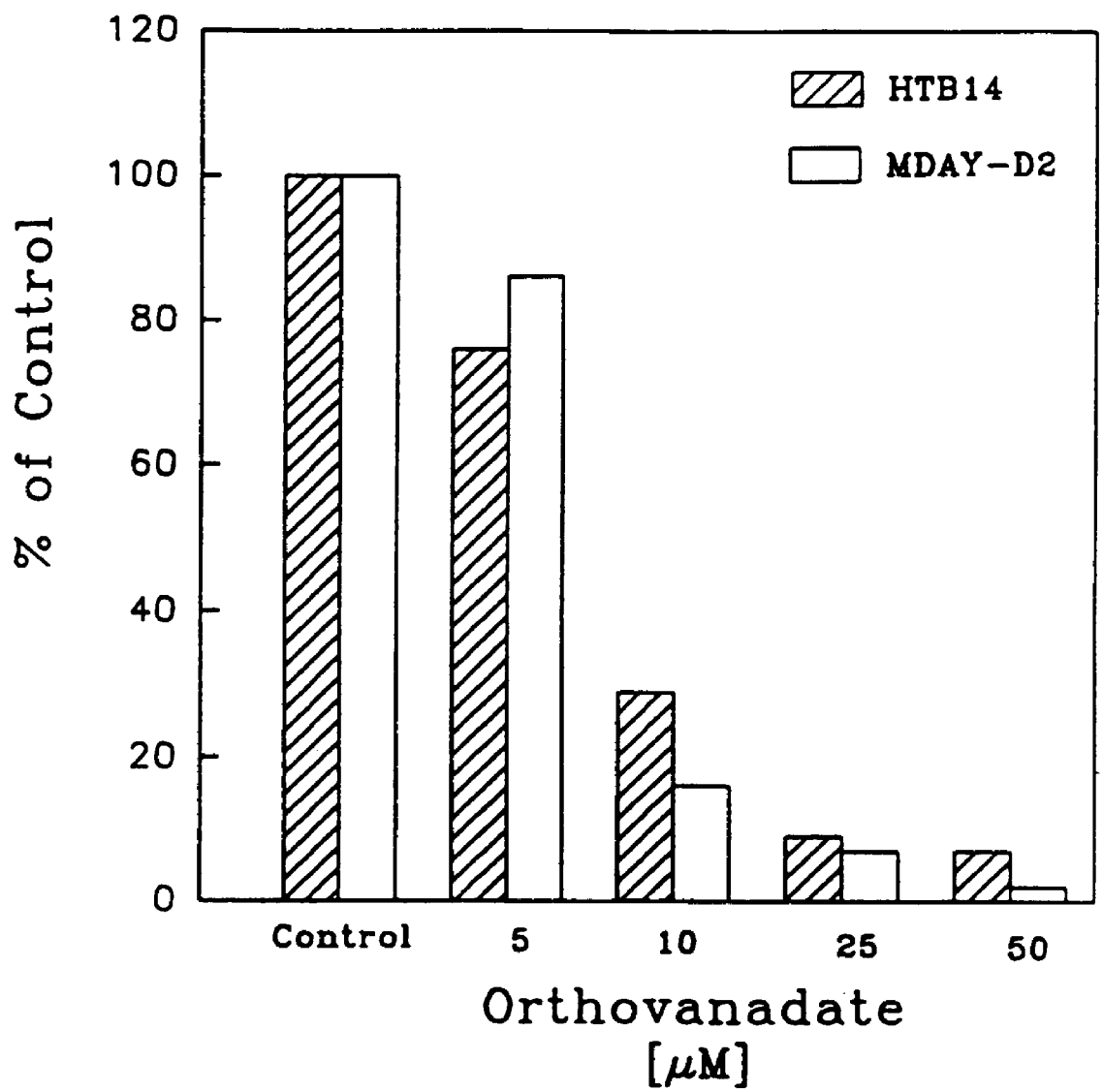
FIG. 7 is a graph showing that orthovanadate is toxic to MDAY-D2 and HTB14 cells.

Fos and jun activity are also required for cellular proliferation in many tumor cell lines. Accordingly, the effect of orthovanadate on adherent cells and cell suspensions were examined. MDAY-D2 (a mouse lymphoid cell line grown in suspension) and HTB14 cells (an adherent human primary astrocytoma cell line) were incubated in media containing 0–50 $\mu$M orthovanadate for 48 hours. The cells were harvested and the number of viable cells determined. FIG. 7 demonstrates the effect of orthovanadate on HTB14 and MDAY-D2 cells.

Orthovanadate treatment resulted in a concentration dependent increase in cell death. Although there were slight differences in sensitivity to orthovanadate between cell types, all cell lines examined were killed by orthovanadate at concentrations of 5 to 10 times lower than that used in the studies with normal nonproliferating cells (above). Orthovanadate induced cell death was observed by 24 hours and complete (over 98%) within 3 days of continuous treatment. In conclusion, treatment of cancer cell lines with orthovanadate leads to cell death at concentrations which had no significant toxic effects on normal non-proliferating cells.

Example 3

Efficacy of Different Forms of Orthovanadate

Figure 8:
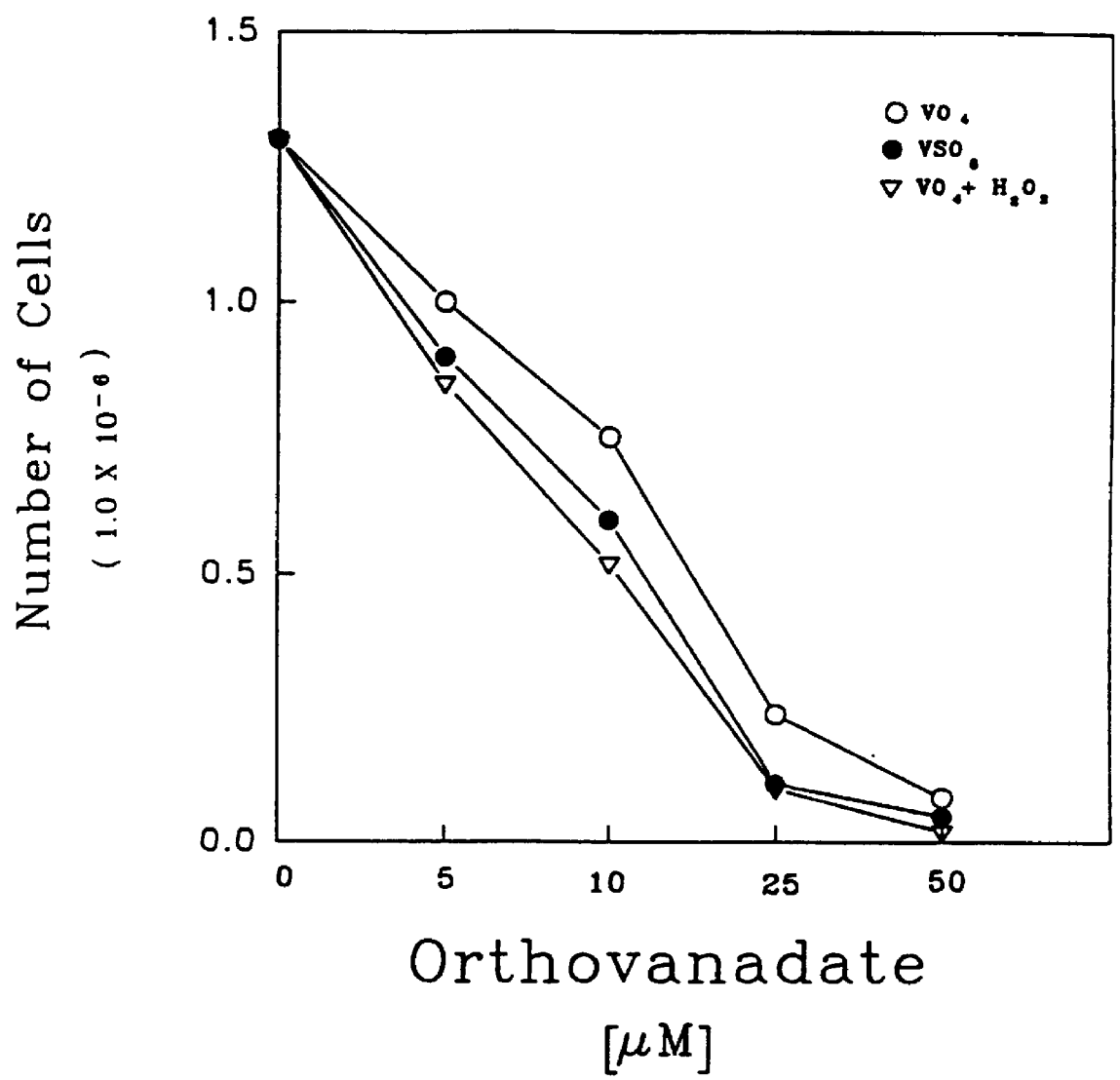
FIG. 8 Is a graph showing the effect of different forms of orthovanadate on cell toxicity.

Three different forms of vanadyl compounds were examined for their effect on viability of cancer cell lines. MDAY-D2 cells were incubated in media containing 0–50 $\mu$M orthovanadate, vanadyl sulphate, or vanadyl hydroperoxide for 48 hours. The cells were harvested and the number of viable cells determined. FIG. 8 demonstrates the effect of orthovanadate, vanadyl sulphate, and vanadyl hydroperoxide on MDAY-D2 cells. The results show that all of these agents were equally effective in killing these cells. Although there were slight differences in sensitivity, the overall cell death was similar.

Example 4

Figure 9:
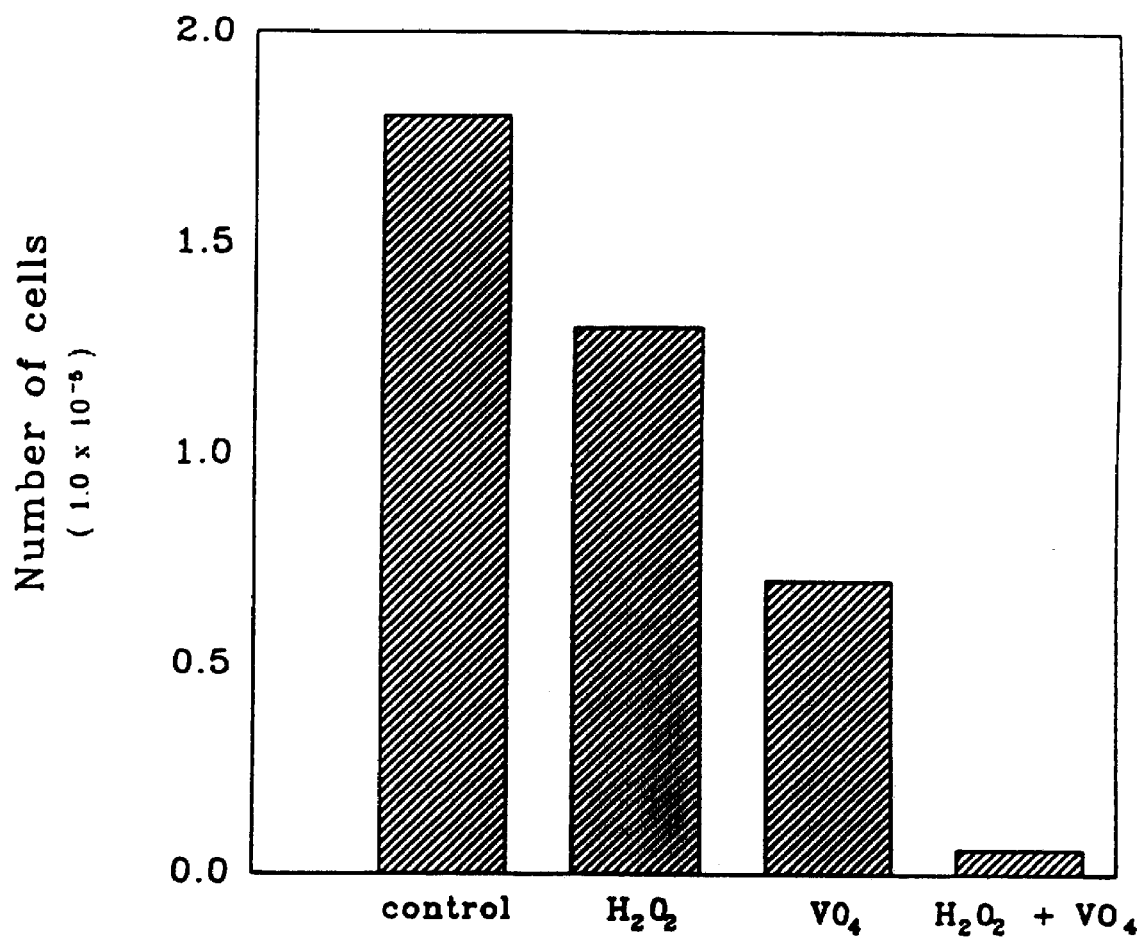
FIG. 9 is a bar graph showing that $H_2O_2$ potentiates orthovanadate toxicity.

Orthovanadate was thought in view of the investigations described in Examples 1–3, to react with $H_2O_2$ to form hydroxyl radicals which are extremely toxic. If the orthovanadate induced formation of hydroxyl radicals is responsible for cell toxicity, then adding exogenous $H_2O_2$ should enhance the effects of orthovanadate. Accordingly, cells were incubated in media alone or containing 1 mM $H_2O_2$ or 10 $\mu$M orthovanadate or both for 24 hours. The cells were harvested and cell viability determined. FIG. 9 demonstrates the combined effects of low concentrations of orthovanadate and $H_2O_2$ on cell toxicity. Addition of $H_2O_2$ alone had a small effect. However, addition of $H_2O_2$ in combination with orthovanadate increased cell toxicity significantly in comparison to orthovanadate alone. The potentiation of cell toxicity by $H_2O_2$ suggests that hydroxyl free radicals generated by orthovanadate treatment may be responsible for the cell death.

Example 5

Orthovanadate is Toxic to Drug Resistant Cell Lines

In many different cancers, tumor cells cannot be eliminated by the conventional chemotherapeutic agents and these tumors are designated drug resistant. Although the mechanisms involved in this process are not well understood, it is thought that these cancer cells express a protein which removes the drug from inside-the cell and reduces its intracellular toxicity. Patients having a drug resistant tumor have a very poor prognosis. Thus, agents which would be toxic to drug resistant tumors would be a valuable chemotherapeutic agent for the treatment of these patients.

Figure 10:
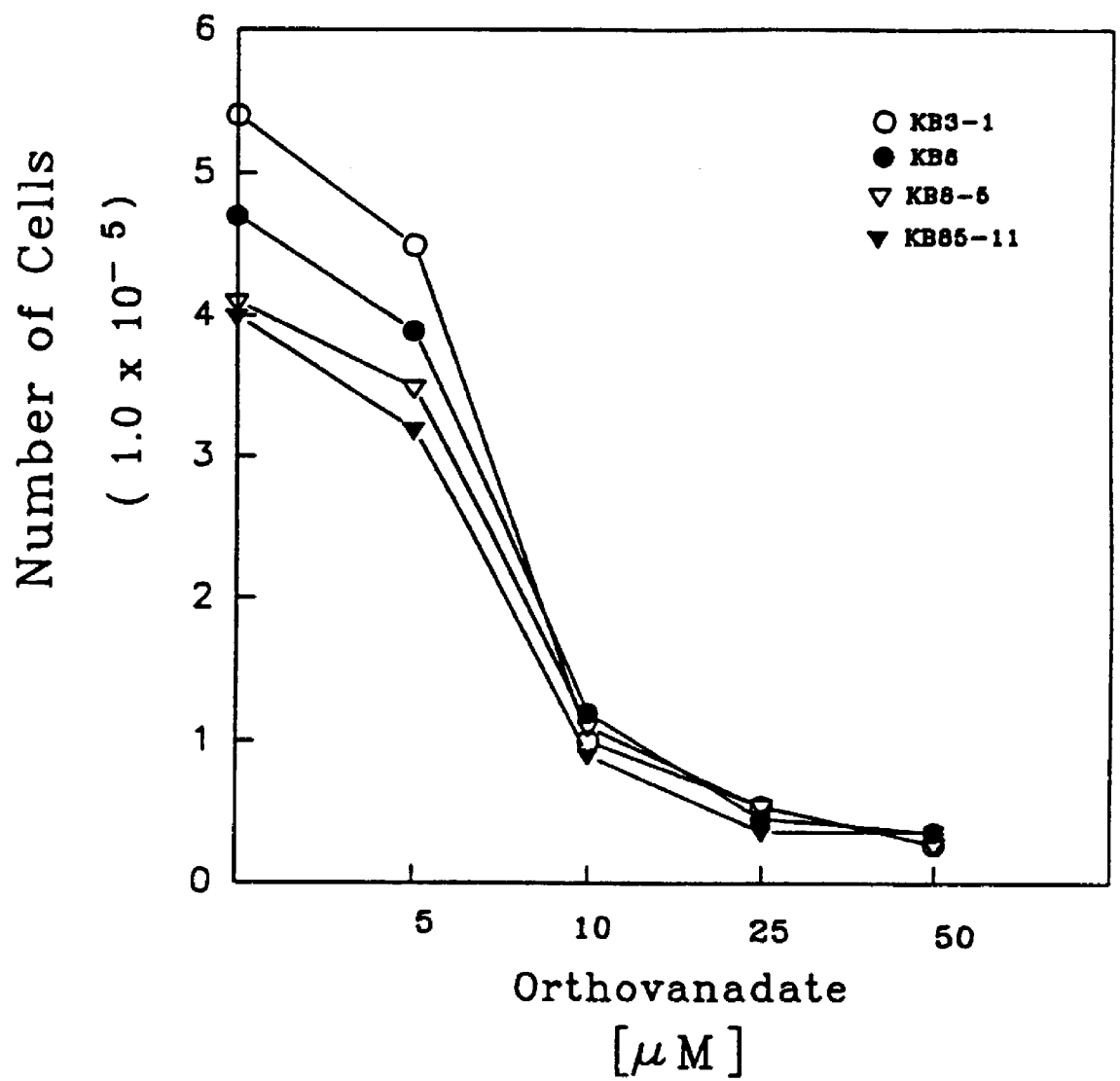
FIG. 10 is a graph showing that orthovanadate is toxic to cell lines of varying drug resistance.

The effect of orthovanadate on three ovarian cancer cell lines, KB8, KB8-5 and KB85-11, which have increasing drug resistance, respectively, relative to the parent cell line, KB3-1 was compared. These drug resistant cell lines are not killed by several classes of chemotherapeutic agents such as colchicine, vinblastine and doxorubicin. In the study, cell lines of increasing drug resistance (KB8, KB8-5 and KB-85-11) and the parent cell line, KB3-1, were incubated in media (DMEM) containing 0–50 $\mu$M orthovanadate for 48 hours. The cells were harvested and the number of viable cells determined. As demonstrated in FIG. 10, orthovanadate was equally effective in killing all of the drug resistant cell lines. Minor differences in sensitivity to orthovanadate was observed between cell lines, but it was not dependent on their drug resistance property, and by three days of orthovanadate administration these differences were not apparent since most of the cells had died.

In conclusion, the data indicate that orthovanadate is lethal to drug resistant cell lines and it may be particularly useful for the treatment of drug resistant tumors.

Example 6

In Vivo Effects of Treatment with Vanadyl Compounds

Figure 11:
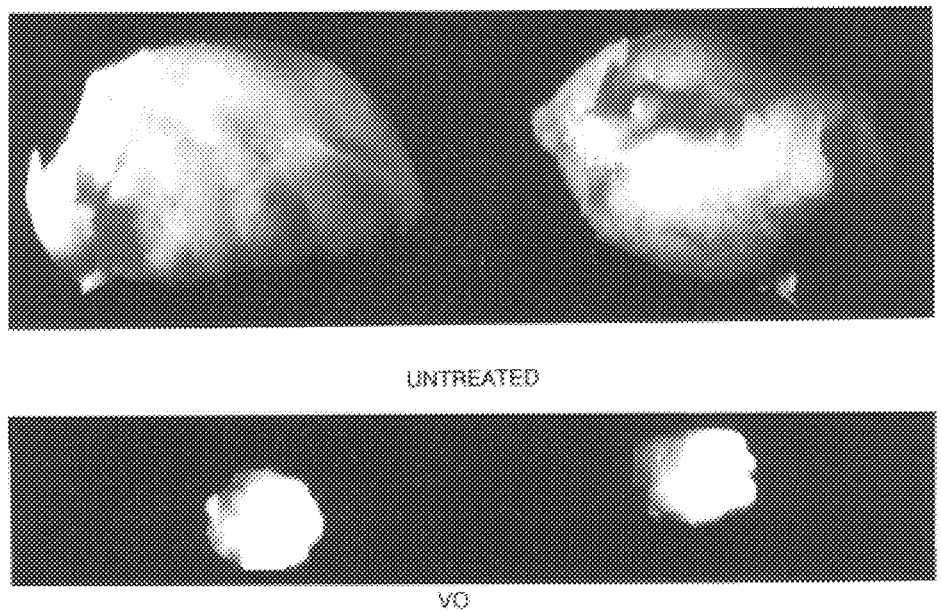
FIG. 11 is a photograph of tumors from untreated and orthovanadate treated mice.
Figure 12:
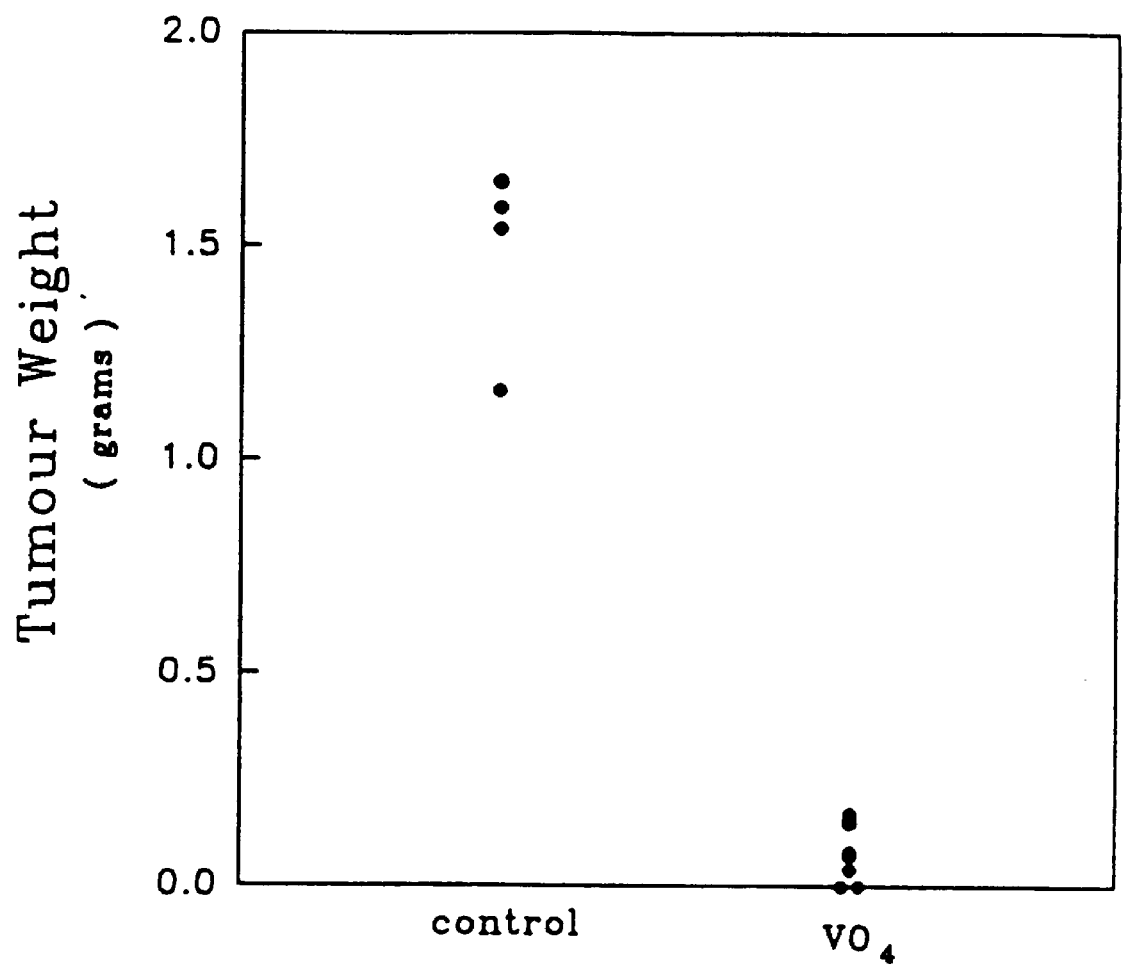
FIG. 12 is a graph showing that orthovanadate administration suppresses tumor growth in vivo.

In order to examine the ability of vanadyl compounds to reduce tumor formation, growth and metastases, a specific animal model which allows investigation of all of these processes in the same animal was chosen. This model involves the injection of a metastatic haematopoietic cell line, MDAY-D2, into mice subcutaneously. These cells form a tumor at the site of injection and its size can be easily determined. In addition, these cells metastasize to the liver and metastases can be detected histologically after day 17 to 19. This model provides a very sensitive and reproducible approach to investigate the effect of vanadyl compounds on tumor growth and metastases.
A. Effect of orthovanadate treatment on tumor growth in vivo Using the animal model described above, the effect of subcutaneous administration of orthovanadate on tumor growth was investigated. A total of 15 mice were injected subcutaneously with $1\times10^5$ MDAY-D2 cells on Day 1. On Day 5, small tumors could be observed at the site of injection. Five mice were injected daily with 50 $\mu$l of water alone and 10 mice were injected daily with water containing 10 mg/ml orthovanadate. On day 14, the mice were sacrificed. The tumors were removed from all the animals, photographed, and weighed. FIG. 11 compares sizes of tumors from two untreated and two orthovanadate treated mice. The tumors of orthovanadate treated mice were either undetectable or considerably smaller. FIG. 12 demonstrates the size of the tumors for each mouse. In animals treated with water alone, four mice had tumors weighing between 1.18 and 1.68 gms. In the orthovanadate treated mice, 2 mice did not have detectable tumors and five mice had tumor sizes that were less than 0.16 gms.
B. Efficacy of orthovanadate, vanadyl sulphate and vanadyl hydroperoxide administration on reducing tumor growth in vivo In a separate experiment using the same animal model, the effect of orthovanadate, vanadyl sulphate and vanadyl hydroperoxide administration on tumor growth in vivo was examined. On Day 1, 20 mice were injected with $2\times10^5$ MDAY-D2 cell subcutaneously. The mice were divided into four groups of five mice. At day 5, the animals were injected subcutaneously with 50 $\mu$l of water alone or containing 10 mg/ml of orthovanadate, 10 mg/ml of vanadyl sulphate, or 10 mg/ml of vanadyl hydroperoxide. This treatment was continued daily for 16 days. At day 21, the mice were sacrificed and the tumors dissected and weighed. One animal died in each of the orthovanadate and vanadyl sulphate treated groups, and all five died in the vanadyl hydroperoxide treated group.

Figure 13:
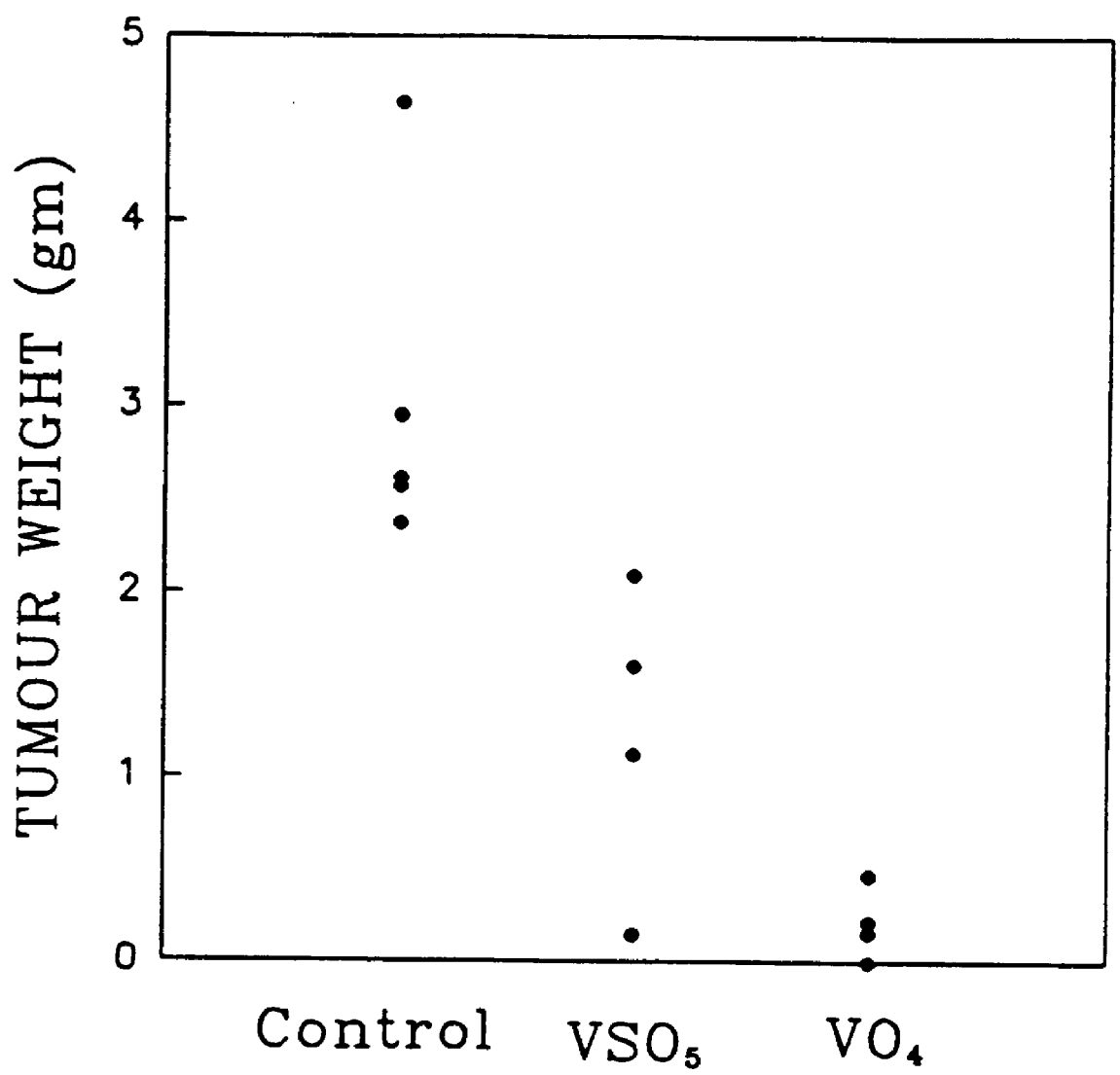
FIG. 13 is a graph showing the effect of orthovanadate, vanadyl sulphate and vanadyl hydroperoxide administration on tumor growth in vivo.

As demonstrated in FIG. 13, the untreated mice developed tumors which ranged in weights from 2.32 to 4.79 gms. Although the effects of vanadyl sulphate treatment were quite variable, the treatment reduced tumors size in all of the animals. The tumors ranged in size from 0.14 gms to 2.18 gms. In the orthovanadate treated group, one mouse did not have detectable tumors and the remaining three mice had tumors which varied in size from 0.15 to 0.38 gms. These data indicate that orthovanadate had the most efficacy in reducing tumor growth, vanadyl sulphate was less effective and vanadyl hydroperoxide was too toxic to evaluate its efficacy.

Example 7

Combination Therapy of Orthovanadate and R-Acetylcysteine Completely Inhibited Tumor Growth and Formation The studies described in the previous examples indicated that orthovanadate was 80 to 100% effective in preventing tumor growth in mice. Since N-acetylcysteine is converted to glutathione in cells, higher levels of glutathione may not only reduce orthovanadate induced toxicity but may also reduce tumor formation. Thus, whether administration of N-acetylcysteine in combination with orthovanadate was more effective in reducing animal toxicity and tumor growth in vivo was examined.

Twenty mice were injected subcutaneously with $2\times10^5$ cells on Day 1. At day 4, the mice were divided into four groups of five mice. Group one (control) received subcutaneous injections of 50 $\mu$l of water. Group two received daily intraperitoneal injections of 50 $\mu$l of 250 mM N-acetylcysteine. Group three received daily subcutaneous injections of 50 $\mu$l of 10 mg/ml of orthovanadate. Group four received daily intraperitoneal injections of 50 μl of 250 nM N-acetylcysteine and 20 minutes later received 50 μl of subcutaneous injection of 50 μl of 10 mg/ml of orthovanadate. On day 10 the treatment was stopped. The animals were sacrificed on Day 13 and analyzed for tumor growth. One orthovanadate treated animal died during the experiment.

Figure 14:
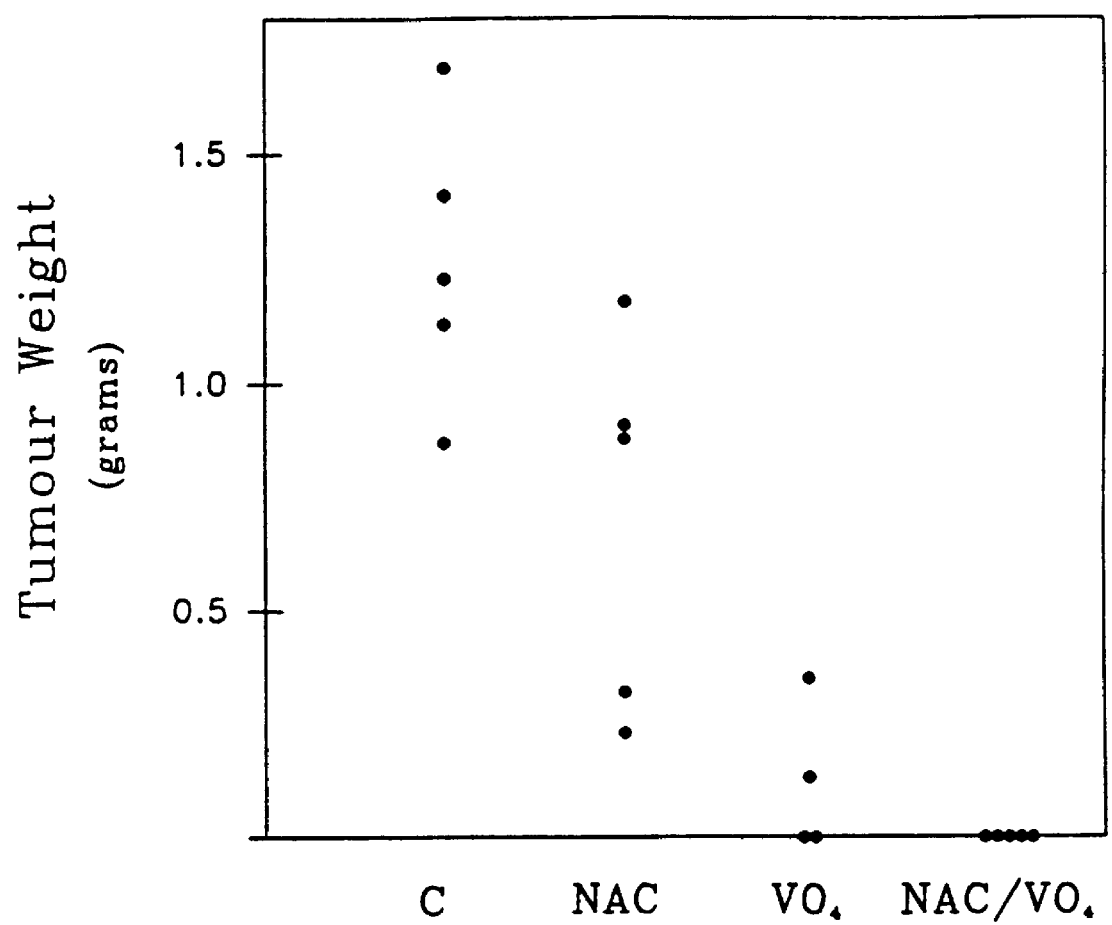
FIG. 14 is a graph showing that orthovanadate and N-acetylcysteine administration completely inhibits tumor growth in vivo.

Tumors were dissected from control mice and mice treated with orthovanadate (VO4) or N-acetylcysteine (NAC) or both (NAC/VO4). The data shown in FIG. 14 represent the weight of each tumor. As demonstrated in FIG. 14, the untreated mice had tumors which weighed between 0.87 to 1.69 gms. In comparison, N-acetylcysteine treated mice had tumors which weighed between 0.23 to 1.18 gms, indicating that this agent alone was capable of reducing tumor growth to some extent. Of the four orthovanadate treated mice, two had no detectable tumors and the other two had tumors weighing 0.13 and 0.35 gms. On the other hand, all five animals receiving orthovanadate and N-acetylcysteine administration had no detectable tumors. These experiments clearly indicated that the combination therapy of orthovanadate and N-acetylcysteine was the most effective therapy in inhibiting tumor growth in vivo. Furthermore, N-acetylcysteine appeared to reduce the slight toxic effects observed in animals treated with orthovanadate alone.

Example 8

Vanadyl Compounds as Anti-Metastatic Agents

Figure 15:
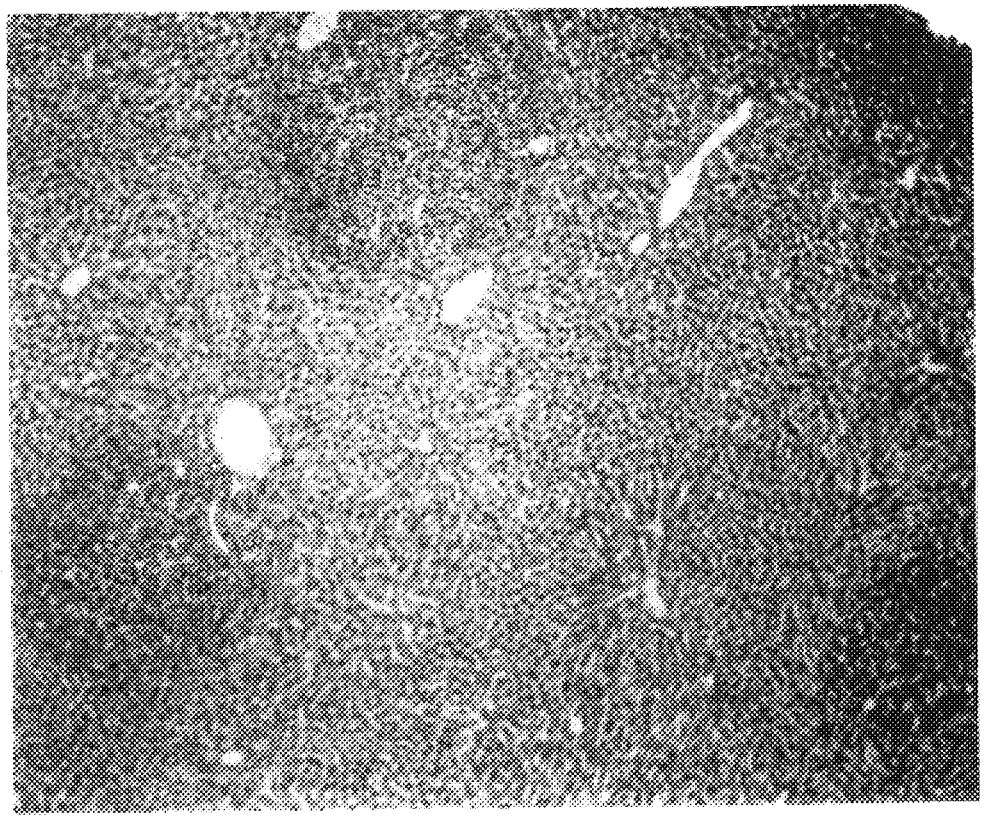
FIG. 15 is a photograph showing liver metastases by MDAY-D2,cells.

Vanadate compounds were found to inhibit metastatic potential of cancer cells by reducing their ability to invade other organs. More particularly, metastases of MDAY-D2 cells was found to occur in the animal model described in Example 6. FIG. 15 shows a control liver and a liver with metastases. The metastatic liver was obtained from an animal 24 days following the administration MDAY-D2 cells. The nodules are quite numerous and large. In animals sacrificed between 19 and 23 days, the number and size of the nodules were quite variable from animal to animal, indicating that in order to examine the anti-metastatic potential of orthovanadate, animals should be maintained for a minimum of 23 days following the injection of MDAY-D2 cells.

Figure 16A:
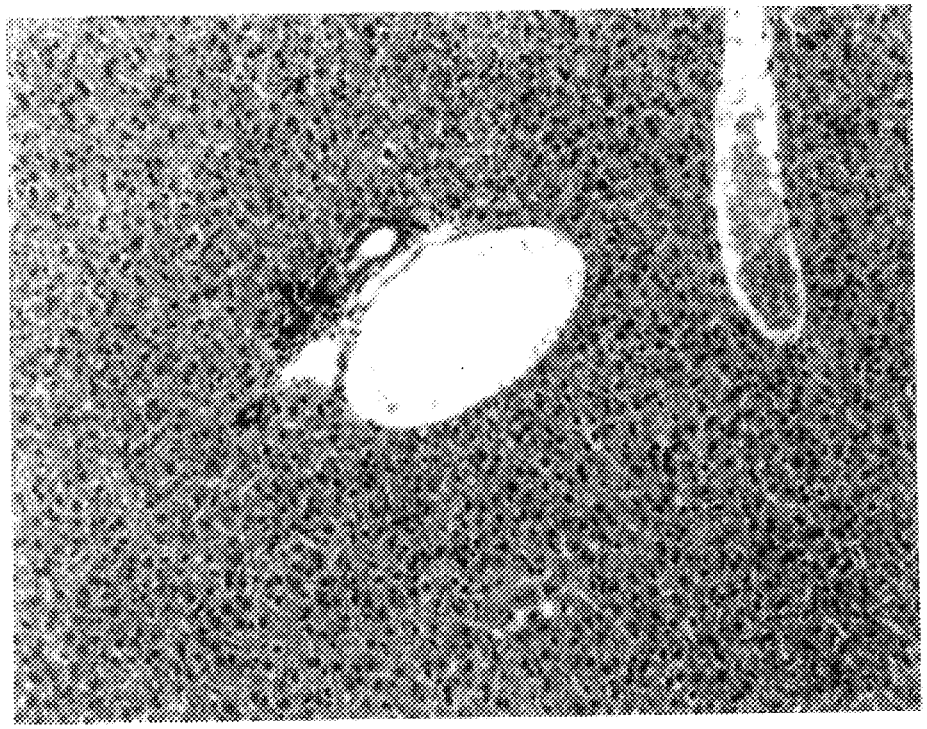
FIG. 16A is a photograph showing the effect of vanadyl sulphate on metastases.
Figure 16B:
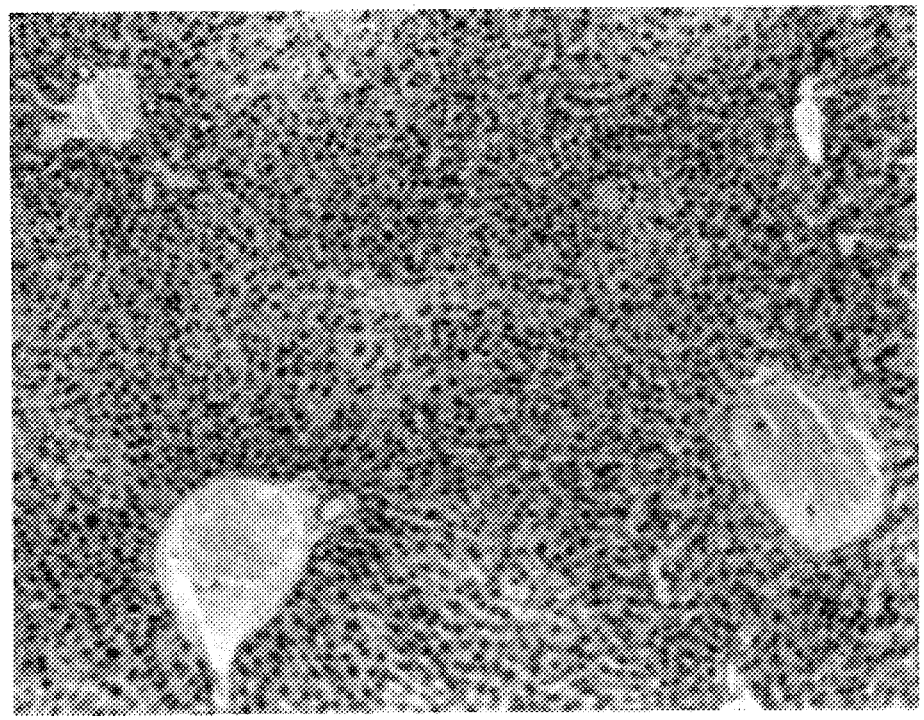
FIG. 16B is a photograph showing the effect of orthovanadate on metastases.
Figure 16C:
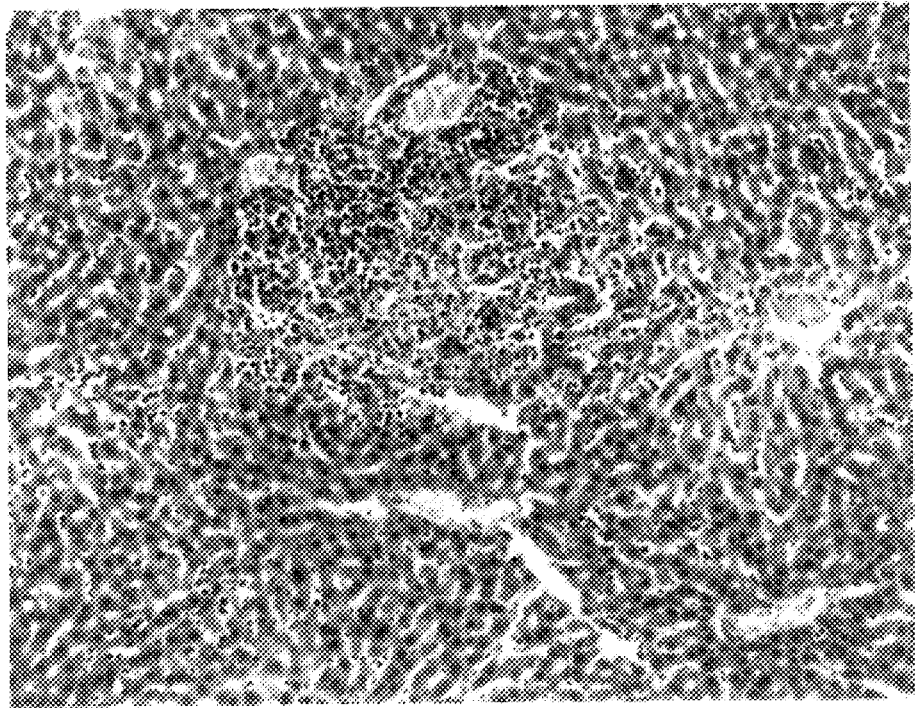
FIG. 16C is a photograph showing the control for the experiments illustrated in FIG. 16A and 16B.

Preliminary results from histological examination of livers obtained following one of the experiments described above in Example 6 suggested that orthovanadate and vanadyl sulphate were both effective at preventing metastases. Livers were removed from animals treated as described above and prepared for histological examination. FIG. 16 compares liver sections from untreated (C), orthovanadate (VO)(500 μg/day) and vanadyl sulphate (VS)(500 μg/day) treated animals. Nodules are identified with an arrow. Infiltration of MDAY-D2 calls and the formation of colonies was observed in the untreated animals. Animals receiving orthovanadate and vanadyl sulphate did not have detectable levels of metastases.

Example 9

Oral administration of orthovanadate at 0.5 mg/ml was found to result in gastric toxicity in laboratory mice. Furthermore intraperitoneal administration of high doses of orthovanadate was also found to be toxic to the animals. However, subcutaneous injections of up to 500 μgms orthovanadate is tolerated by the animals. Slow administration of the orthovanadate would decrease toxicity and the animals may tolerate higher doses.

Example 10

Comparison with Kaplan U.S. patent Ser. No. 5, 045,316

The concentration of vanadate used by Kaplan was found to be far too low to be effective in inhibiting tumor growth or metastases. In order to determine whether Kaplan's optimum conditions were effective, the effect of the highest concentrations of orthovanadate alone, or thiosulfate alone, or orthovanadate and thiosulfate administered together on tumor growth in mice was investigated. Kaplan reported daily doses ranging from 0.0043 mg/kg to 0.14 mg/kg of vanadyl or vanadate salts are required for treatment. Assuming an equal distribution in the body fluids and a water content of 56%, the maximum concentration of orthovanadate in the serum with these doses at the time of administration is from 0.04 μM to 1.3 μM.

Figure 17:
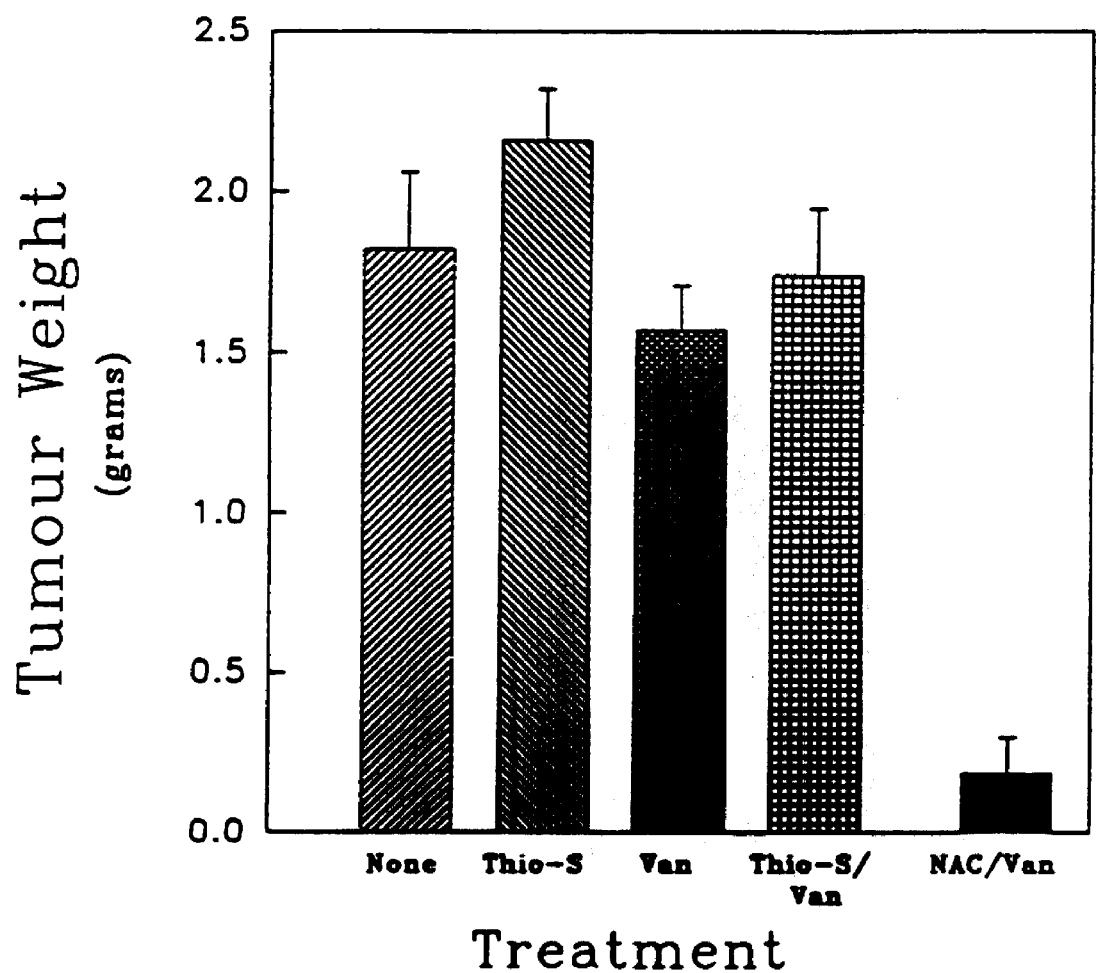
FIG. 17 is a graph showing a comparison of a prior art treatment and the orthovanadate/N-acetylcysteine treatment of the present invention.

As demonstrated in FIG. 17, no decrease in tumor growth was observed with any of the agents described by Kaplan alone, or in combination, at the doses disclosed by Kaplan. Under the optimum treatment conditions of the present invention, tumor growth was either not apparent or less than 80% of control.

From the foregoing, it will be appreciated that, although specific embodiments of the invention have been described herein for purposes of illustration, various modifications may be made without deviating from the spirit and scope of the invention. Accordingly, the invention is not limited except as by the appended.

We claim:

1. A method for reducing or inhibiting the growth of a drug resistant tumor in a patient comprising administering to the patient a pharmaceutical composition consisting essentially of an amount of a vanadate or vanadyl compound effective to reduce or inhibit the growth of the drug resistant tumor and a pharmaceutically acceptable vehicle.

2. A method as claimed in claim 1 wherein the drug resistant tumor is an ovarian, breast, or hematopoietic tumor.

3. A method for reducing metastases in a patient comprising administering to the patient a pharmaceutical composition consisting essentially of an amount of a vanadate or vanadyl compound effective to reduce metastases and a pharmaceutically acceptable vehicle.

4. A method as claimed in claim 3 for reducing metastases of a lung, lymphoid, or an astrocytoma primary tumor.

5. A pharmaceutical composition for use in reducing tumor cell proliferation, consisting essentially of a vanadate or vanadyl compound and at least one antioxidant, and one or more of a pharmaceutically acceptable carrier, diluent, or excipient wherein the pharmaceutical composition is adapted for administration to a patient in vivo, and the vanadate or vanadyl compound is present in an amount which provides a serum concentration of the compound in the patient of at least 5 μM.

6. A composition as claimed in claim 5, wherein the vanadate compound is orthovanadate and the antioxidant is N-acetylcysteine.

7. A method for reducing tumor cell proliferation in a mammal, comprising administering a pharmaceutical composition as claimed in claim 6 consisting essentially of an effective amount of a vanadate or vanadyl compound and at least one antioxidant.

8. The method as claimed in claim 7 wherein the vanadate or vanadyl compound is orthovanadate or vanadyl sulphate.

9. The method as claimed in claim 7 wherein the antioxidant is N-acetylcysteine, glutathione, Vitamin E (alpha-tocopherol), Vitamin C (ascorbic acid), beta-carotene, ergothioneine, zinc, selenium, copper, manganese, a flavonoid or an estrogen.

10. The method as claimed in claim 9 wherein the vanadate or vanadyl compound is administered at a dose which provides a serum concentration of at least 5 $\mu$M and the N-acetylcysteine is administered at a dose which provides a serum concentration of between 0.5 mM to 15 mM.

* * * * *